United States Patent
Wu et al.

(10) Patent No.: US 7,444,875 B1
(45) Date of Patent: Nov. 4, 2008

(54) REAL TIME VISUALIZATION OF SHEAR WAVE PROPAGATION IN SOFT MATERIALS WITH SONOELASTOGRAPHY

(75) Inventors: Zhe Wu, New Berlin, WI (US); Kevin J. Parker, Rochester, NY (US)

(73) Assignee: University of Rochester, Rochester, NY (US)

( * ) Notice: Subject to any disclaimer, the term of this patent is extended or adjusted under 35 U.S.C. 154(b) by 436 days.

(21) Appl. No.: 11/356,472

(22) Filed: Feb. 17, 2006

Related U.S. Application Data

(60) Provisional application No. 60/653,987, filed on Feb. 18, 2005.

(51) Int. Cl.
*A61B 8/00* (2006.01)
*A61B 5/103* (2006.01)

(52) U.S. Cl. ............... 73/602; 600/438; 600/443

(58) Field of Classification Search .......... 73/602; 600/438, 443
See application file for complete search history.

(56) References Cited

U.S. PATENT DOCUMENTS

| | | | |
|---|---|---|---|
| 5,810,731 A * | 9/1998 | Sarvazyan et al. ...... 600/438 |
| 6,561,981 B2 * | 5/2003 | Bonnefous ............ 600/443 |
| 6,770,033 B1 * | 8/2004 | Fink et al. ............ 600/443 |
| 2004/0068184 A1 * | 4/2004 | Trahey et al. .......... 600/437 |
| 2005/0054930 A1 * | 3/2005 | Rickets et al. .......... 600/453 |
| 2005/0252295 A1 * | 11/2005 | Fink et al. ............. 73/603 |

OTHER PUBLICATIONS

Wu, et al., "Sonoelastographic Imagining of Interference Patterns for Estimation of the Shear Velocity of Homogeneous Biomaterials," Inst. of Physics Publishing, Phys. Med. Biol. 49 (2004), pp. 911-922.
Wu, et al., "Shear Wave Interferometry and Holography, an Application of Sonoelastography," School of Engineering and Applied Sciences, University of Rochester, 2005.

* cited by examiner

*Primary Examiner*—Hezron Williams
*Assistant Examiner*—Rose M Miller
(74) *Attorney, Agent, or Firm*—Blank Rome LLP

(57) ABSTRACT

An ultrasound system visualizes shear wave propagation in real time by slowing down the propagation of the shear wave as seen by the ultrasound probe. The shear wave source propagates shear waves into the medium at a frequency $\omega$. The ultrasound probe is vibrated by a vibrator at the frequency $\omega-\Delta\omega$, where $\Delta\omega$ is much smaller than $\omega$. The wave propagation as seen by the ultrasound probe is slowed down by a factor $\Delta\omega/\omega$. An appropriate value of $\Delta\omega$ allows real-time visualization of the wave propagation. Variations include electronically producing a virtual vibration and the use of multiple shear wave sources.

32 Claims, 8 Drawing Sheets

REAL TIME VISUALIZATION OF SHEAR WAVE PROPAGATION IN SOFT MATERIALS WITH SONOELASTOGRAPHY

REFERENCE TO RELATED APPLICATION

The present application claims the benefit of U.S. Provisional Patent Application No. 60/653,987, filed Feb. 18, 2005, the disclosure of which is hereby incorporated by reference in its entirety into the present disclosure.

STATEMENT OF GOVERNMENT INTEREST

The work leading to the present invention was supported by the National Institutes of Health under Grant No. 2R01 AG16317-01A1. The government has certain rights in the invention.

FIELD OF THE INVENTION

The present invention is directed to a technique for sonoelastography and more particularly to such a technique in which shear waves are caused to interfere to produce a stationary or slowly moving wave from which the shear wave velocity can be determined.

DESCRIPTION OF RELATED ART

It is widely accepted that the changes in elasticity of tissues are possible markers of certain diseases. In modern medicine, digital palpation is a routine screening method in physical examinations. One approach to examine the tissues' local elasticity is to visualize the local behavior of shear waves excited by internal or external sources.

A common approach to doing so is through an ultrasonic imaging modality called sonoelastography. Sonoelastography estimates the peak displacements of particle motion under audio frequency excitations by analyzing the power spectrum variance of the ultrasound echoes, which is proportional to the local vibration amplitude. Vibration fields are then mapped to a commercial ultrasound scanner's screen.

However, since the shear wave speed in soft tissues is on the order of a few meters per second, few imaging modalities are able to follow the propagation on a scale of a centimeter or less. The existing techniques to follow the shear wave propagation, either have a very high temporal sampling rate (high frame rate) or carefully subsample the propagation progressively (also known as the strobe effect). Such available systems either require off-line computing or prolonged data acquisition. Therefore, those techniques are not real-time.

SUMMARY OF THE INVENTION

It is therefore an object of the invention to develop such a technique which works in real time.

It is another object of the invention to develop such a technique which is non-invasive.

It is still another object of the invention to develop such a technique which does not require a high frame rate or "strobing."

It is yet another object of the invention to develop such a technique in which the ultrasound scanner can run asynchronously from the vibration, as a normal Doppler imaging sequence.

It is yet another object of the invention to develop such a technique which can be implemented with a single shear wave source.

It is yet another object of the invention to develop such a technique which does not assume any particular type of propagation of the shear wave in the medium.

To achieve the above and other objects, the present invention is directed to a technique for visualizing the shear waves in soft tissues in real time in which wave propagations are virtually "slowed down" for observations. The spatial distribution of the shear wave speed can be reconstructed from the wave propagation video and therefore indicates the size and location of the stiff region in the tissue. The present invention provides many of the advantages of magnetic resonate elastography (MRE), but with the additional advantages of real time visualization of the vibration fields.

One shear wave source propagates shear waves into the medium at the frequency $\omega$. An ultrasound (US) probe is held above the surface of the medium. The ultrasound probe is vibrated by a vibrator at the frequency $\omega - \Delta\omega$, where $\Delta\omega$ is much smaller than $\omega$.

The total field estimated by the ultrasound scanner is the shear wave propagation relative to the probe vibration, which is called the modulated field. The modulated field is a representation of the propagating shear wave field, only at a different frequency and thus different velocity. By carefully selecting $\omega$ and $\Delta\omega$, the shear wave propagation can be virtually slowed down so that it can be visualized by sonoelastography.

The present invention is validated in both a homogeneous phantom experiment and an inhomogeneous phantom experiment. The present invention provides many of the advantages of magnetic resonate elastography (MRE), but with the additional advantages of real time visualization of the vibration fields.

Since the present invention can use the existing Doppler hardware on most modern US scanners, the frame rate of sonoelastography is as high as other Doppler modalities. In one example, regions where the vibration amplitude is low are displayed as dark green, while regions with high vibration are displayed as bright green.

The present invention offers a further advantage in that it does not assume any particular type of wave propagation; for example, it does not assume a plane wave. The vibration of the probe is completely temporally dependent and does not interfere with the spatial variation of the propagation of the shear wave. The present invention offers yet another advantage in that only one shear wave source is needed.

Variations include electronically producing a virtual vibration of the probe and the use of multiple shear wave sources.

The following disclosures disclose aspects of the invention and are hereby incorporated by reference in their entireties into the present disclosure:

Zhe Wu et al, "Sonoelastographic imaging of interference patterns for estimation of the shear velocity of homogeneous biomaterials," *Phys. Med. Biol.* 49 (2004) 911-922; and Zhe Wu, "Shear Wave Interferometry and Holography, an Application of Sonoelastography," submitted in partial fulfillment of the requirements for the degree of Doctor of Philosophy, Department of Electrical and Computer Engineering, University of Rochester, Rochester, N.Y., 2005.

BRIEF DESCRIPTION OF THE DRAWINGS

A preferred embodiment of the present invention will be set forth in detail with reference to the drawings, in which.

DETAILED DESCRIPTION OF THE PREFERRED EMBODIMENT

Figure 1:
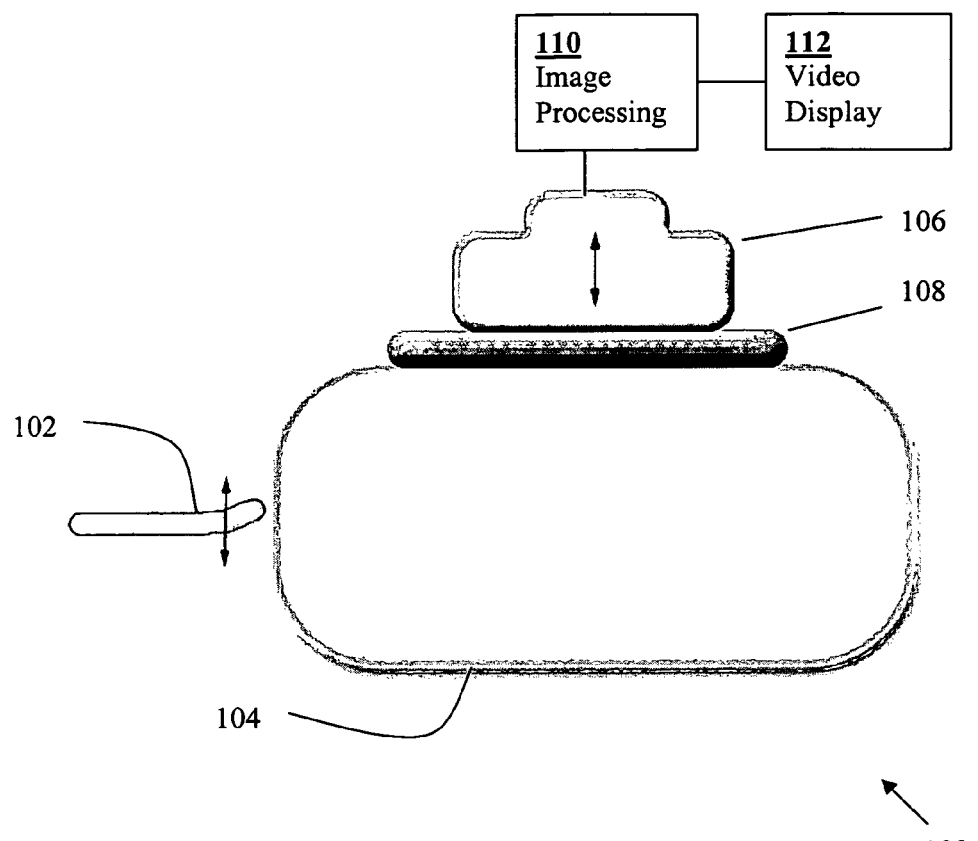
FIG. 1 is a schematic diagram of a system according to the preferred embodiment.

A preferred embodiment of the invention will be set forth in detail with reference to the drawings, in which like reference numerals refer to like elements or steps throughout.

FIG. 1 shows a system 100 according to the preferred embodiment. As shown, the shear wave source 102 vibrates at the frequency ω. Induced by the shear wave source, each particle in the medium 104 oscillates at the same frequency with a spatially dependent phase, the derivative of which is the phase velocity of the shear wave. Assuming that the shear wave source is stationary, the vibration amplitude of each particle in the medium can be written as $f(x)$, where $f(x)$ is a function of x, and x represents the spatial coordinates in two dimensions. In addition, the spatial shape of the shear waves may take any arbitrary form. In other words, the vibration field can be written as:

$$U(x,t) = f(x) * \exp[i(\omega t - s(x))] \tag{1}$$

where s(x) is an arbitrary function subject to the wave equation and boundary conditions.

A wavefront is determined by assigning (ωt−s(x)) to a constant value:

$$\omega t - s(x) = \phi$$

where ϕ is a constant phase.

Taking derivatives on both sides:

$$\omega dt = s'(x) * dx$$

$$v_s = \frac{dx}{dt} = \frac{\omega}{s'(x)} \tag{2}$$

where $v_s$ is the shear wave phase velocity and s'(x) is the first derivative of s(x) with respect to x. s'(x) is the local wave number or the local spatial frequency. Thus, if one can visualize s(x) and its movement over time, then one can determine $v_s$, which is directly linked to the stiffness of tissue:

$$v_s = \sqrt{\frac{G}{\rho}} \tag{3}$$

where G is the shear modulus of the medium 104 and ρ is its mass density.

While transmitting and receiving ultrasound signals, the ultrasound probe 106 is also externally vibrated. The ultrasound probe 106 is carefully positioned above the soft material 104 without touching it. A thick layer of ultrasound gel 108 is applied to couple the acoustic energy into the soft material 104. The ultrasound probe 106 is carefully positioned so that there is always an ultrasound gel filled gap between the probe and the surface of the medium to make sure the vibration of the US probe does not propagate shear waves into the phantom. Signals received by the US probe 106 are processed in an image processing device 110, in a manner to be described below, to produce images that are displayed on a video display 112 or output in any other suitable manner.

The particle motion relative to the ultrasound probe is estimated by the sonoelastography algorithm. The ultrasound probe is vibrated at a frequency ω−Δω, where Δω<<ω. Therefore, the motion of the ultrasound probe is:

$$R(t) = A * \exp[i(\omega - \Delta\omega)t] \tag{4}$$

where A is a constant.

Hence the vibration field relative to the ultrasound probe is:

$$P(x, t) = U(x, t) - R(t) \tag{5}$$

$$= f(x) * \exp[i(\omega t - s(x))] - A * \exp[i(\omega - \Delta\omega)t]$$

The square of P(x,t)'s envelope is:

$$|P(x, t)|^2 = P * P^* \tag{6}$$

$$= [U(x, t) - R(t)] * [U(x, t)^* - R(t)^*]$$

$$= \{f(x) * \exp[i(\omega t - s(x))] - A * \exp[i(\omega - \Delta\omega)t]\} *$$

$$\{f(x) * \exp[-i(\omega t - s(x))] - A * \exp[-i(\omega - \Delta\omega)t]\}$$

$$= f(x)^2 + A^2 - A \cdot f(x) \exp(i\Delta\omega t - is(x)) -$$

$$A \cdot f(x) \exp(-i\Delta\omega t + is(x))$$

$$= f(x)^2 + A^2 - 2A \cdot f(x) \cos(\Delta\omega t - s(x))$$

where P* is the complex conjugate of P.

Since the shear wave is mechanically modulated by the ultrasound probe motion, $|P^2(x,t)|$ is called the modulation wave. Similarly to equation (2), the phase velocity of the modulation wave is $$v_m = \frac{dx}{dt} = \frac{\Delta\omega}{s'(x)} \tag{7}$$

Comparing equation (7) with equation (2) gives:

$$v_m = \frac{\Delta\omega}{\omega} * v_s \tag{8}$$

Also notice that the mechanical modulation does not interfere with the spatial component of equation (1), i.e. s(x). Therefore the exact shear wave appearance is preserved. Apart from a DC shift in the amplitude and a change in the velocity, the shear wave propagation is exactly represented by the modulation wave. Since Δω/ω is an arbitrary and controllable factor, the shear wave can thus be slowed by the mechanical modulation to be studied by ordinary ultrasound scanners with the sonoelastography modifications.

Experimental validation will now be described.

Figure 2:
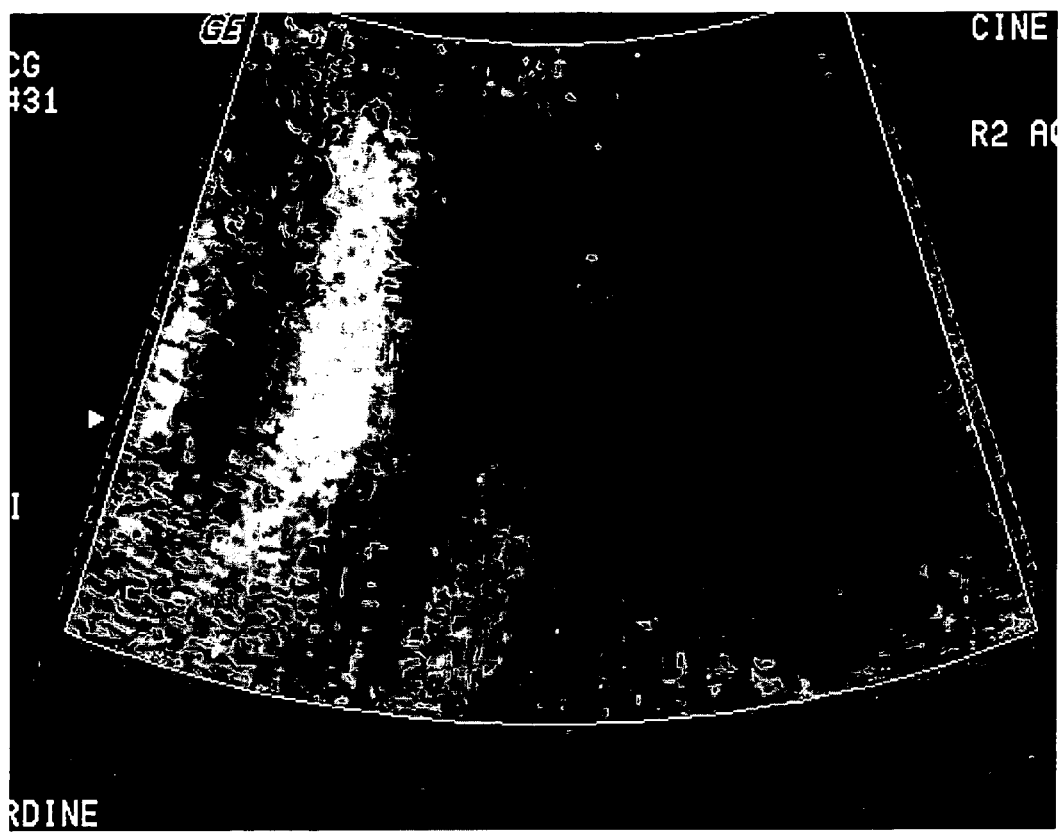
FIG. 2 is a frame of modulation wave propagation as imaged by the system of FIG. 1.

In the validating experiments, a double channel signal generator (Tektronix AFG320) produces two monochrome low frequency signals at slightly different frequencies. One channel of the signals (199.9 Hz) drives a bending piezo elements known as Thunder (Face International Corporation, Norfolk, Va.) which is applied to vibrate the US transducer. The other channel of the signal (200 Hz) drives a shear wave actuator (Piezo System, Massachusetts), which propagates shear waves into a Zerdine (CIRS, Virginia) ultrasound phantom. The phantom has a hard inclusion and is otherwise uniform. A GE Logiq 700, which has been specially modified to implement the sonoelastography functions, is applied to visualize the "modulation wave" propagation. With the realtime visualization, the shear waves are virtually "slowed down" so that the local and subtle behaviors of the waves can be examined closely. The different wave speeds within and outside of the lesion can be perceived by the human eye. One frame of the "modulation wave" propagation is shown in FIG. 2. The shear wave wavefronts are visibly distorted by the hard inclusion and thus the size and the location of the lesion is estimated.

There are a number of existing techniques from MRE and other methods for calculating $v_s$ from $s(x, t)$. Those can be optionally applied to the present invention as post-processing to create images of local $v_s$. As an example, the local frequency estimator (LFE) filter bank estimates the local spatial frequency which is inversely proportional to the local shear wave speed. Because of the low signal to noise ratio (SNR) nature of ultrasonic image acquisition, a series of procedures are proposed to reduce the noise and to increase the SNR. First of all, the local vibration phase at each pixel is estimated from the wave propagation video:

$$\phi(x, y) = \arctan\left(\frac{\mathrm{imag}(\mathcal{P}_{xy}(\Delta\omega))}{\mathrm{real}(\mathcal{P}_{xy}(\Delta\omega))}\right) \quad (9)$$

where $\mathcal{P}_{xy}$ is the Fourier transform of $P_{xy}^2(t)$:

$$\mathcal{P}_{xy} = \mathcal{F}(P_{xy}^2(t)) \quad (10)$$

Figure 3:
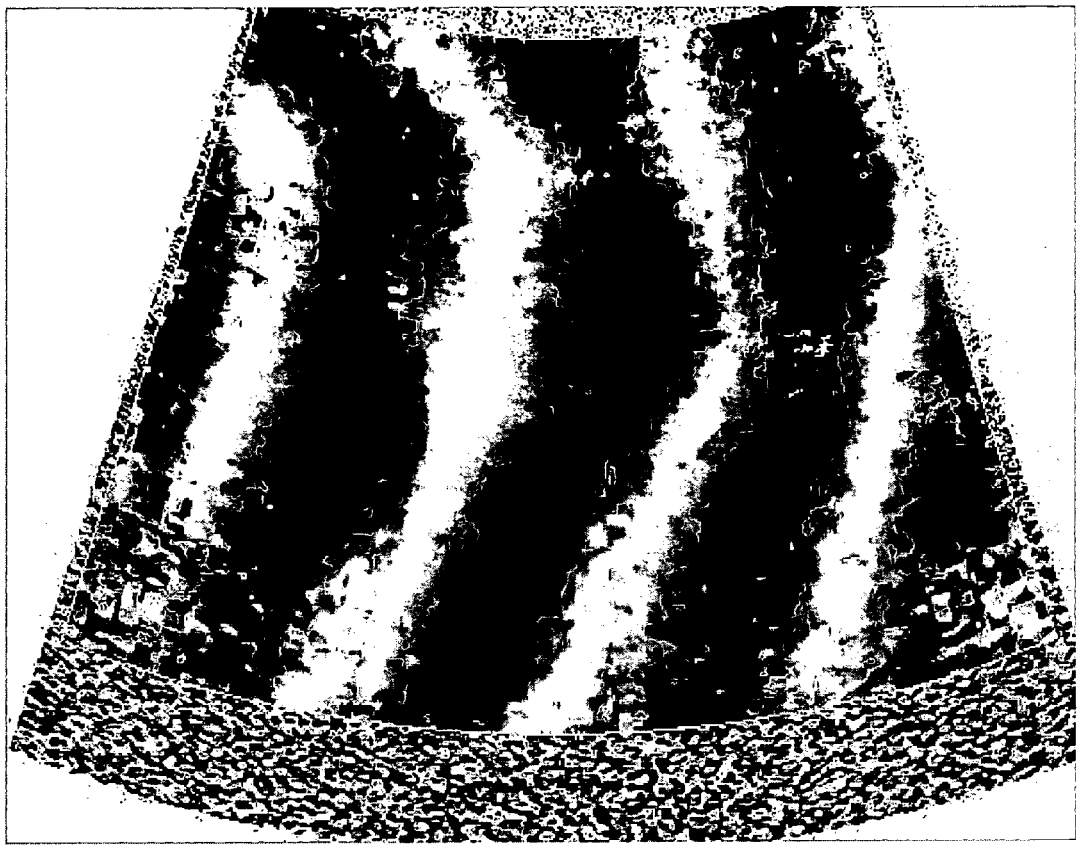
FIG. 3 is an image of a wrapped phase estimation derived in the system of FIG. 1.
Figure 4:
FIG. 4 is an image of an unwrapped phase estimation derived from the wrapped phase estimation of FIG. 3.
Figure 5:
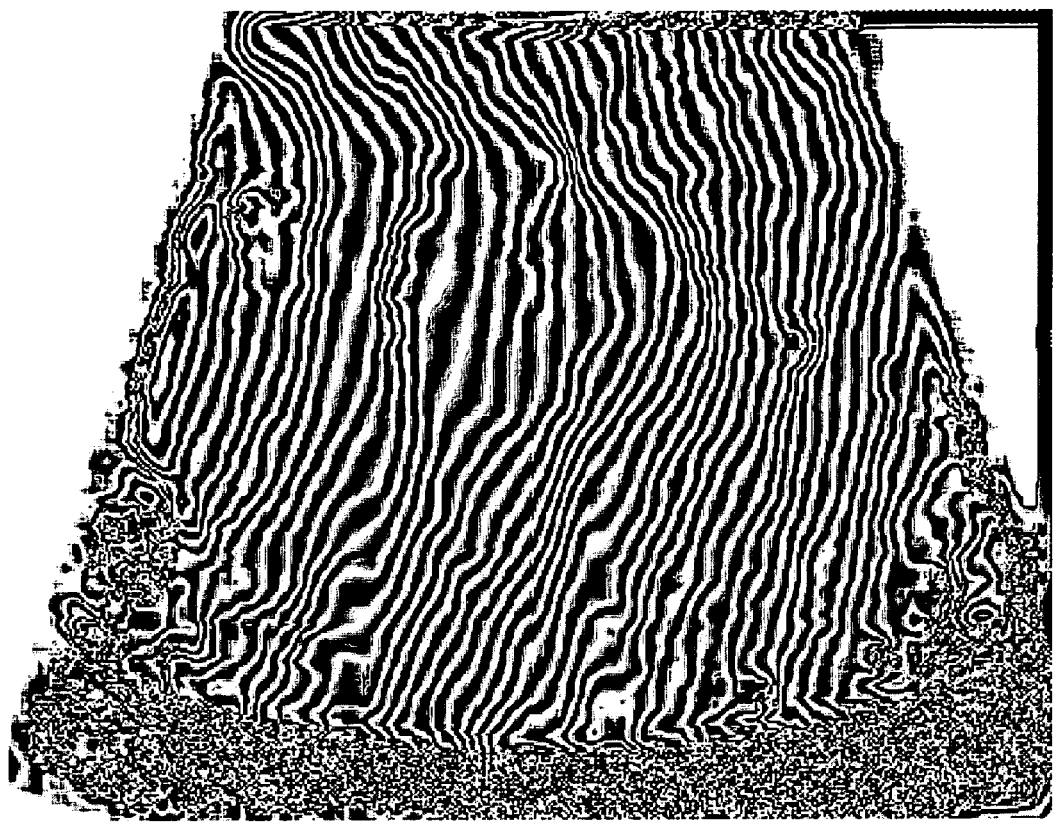
FIG. 5 is an image of a reconstructed wave pattern derived from the unwrapped phase estimation of FIG. 4.
Figure 6:
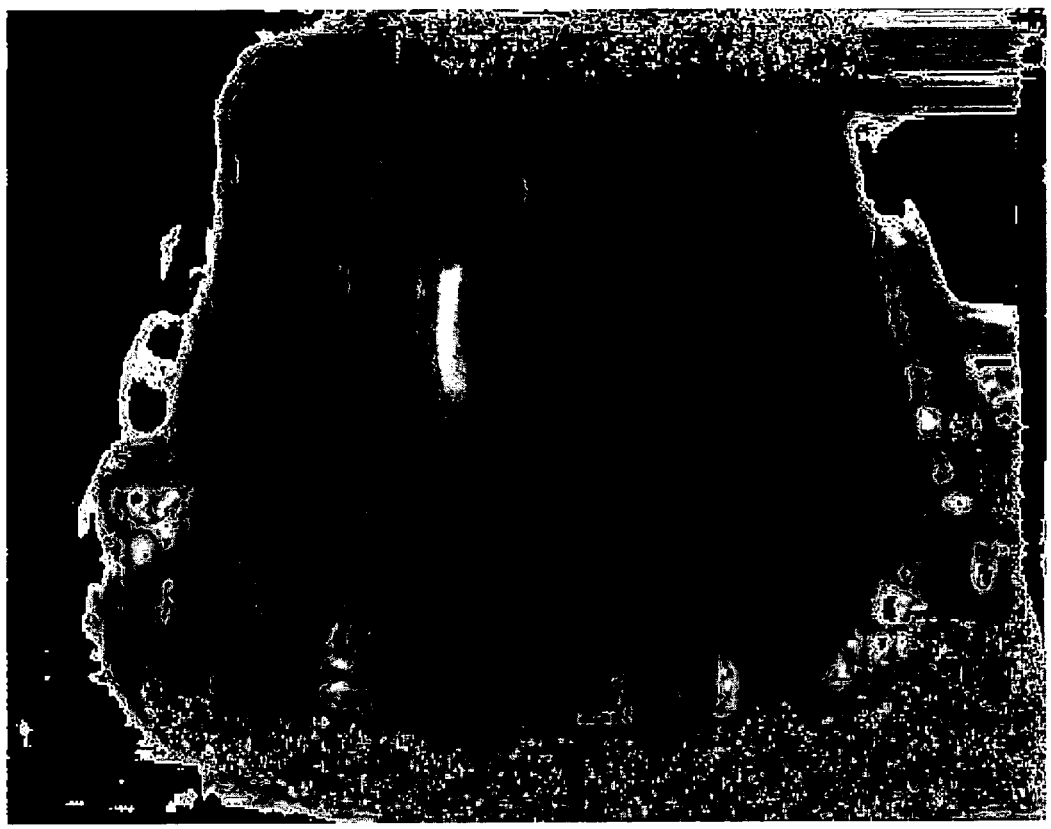
FIG. 6 is an image of a wave speed distribution derived from the reconstructed wave pattern of FIG. 5.

Because the phase estimation results are always between $-\pi$ and $\pi$, a phase unwrapping procedure is necessary to create a smooth phase surface. A wrapped phase estimation is depicted in FIG. 3, and FIG. 4 depicts an unwrapped phase surface. The phase unwrapping procedure eliminates the sharp transitions in the original phase map to ensure that any subsequent noise reduction procedure does not blur the edges. After noise reduction, the unwrapped phase map is converted to the wave patterns with artificially increased spatial density:

$$I(x,y) = \cos(N^*\phi(x,y)) \quad (11)$$

where N is an arbitrary constant, which is typically chosen from 2 to 20. FIG. 5 shows a reconstructed wave pattern with N=12. That operation virtually increases the number of wavefronts per unit area. That reconstruction enhances the visibility of the low spatial frequency area which corresponds to the location of the stiff inclusion. Furthermore, the LFE filter bank is applied over the wave patterns to estimate the local spatial frequency. The local wave speed distribution, which is inversely proportional to the local frequency, is then displayed, as shown in FIG. 6.

The phantom includes an area of high elasticity surrounded by an area of low elasticity. The area of high elasticity is shown in FIG. 5 as an area of low spatial frequency and in FIG. 6 as a bright area surrounded by a dark area. In an organ such as a prostate, a lesion is imaged in the same manner, by imaging the change in elasticity between the lesion and surrounding healthy tissues.

Figure 7:
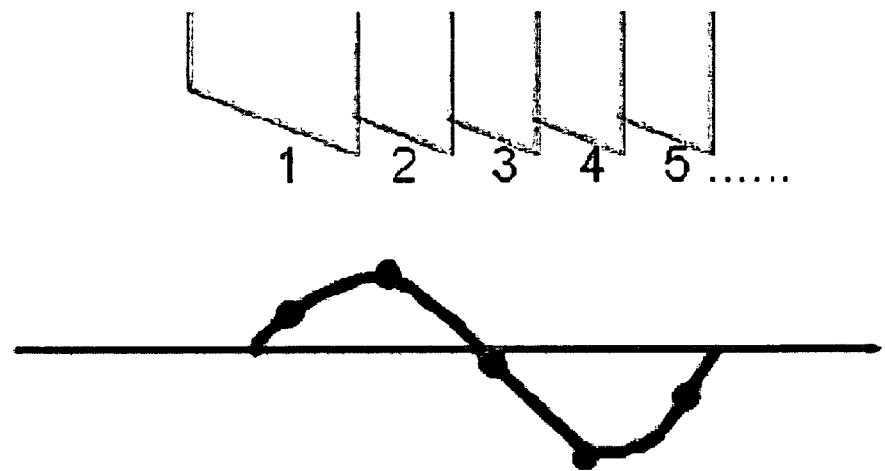
FIG. 7 is a graph showing the time trace of the brightness of a pixel.

The estimator accuracy will now be considered. It will be seen from the above that final estimation results rely extensively on the phase estimation of lical vibration. The local vibration phase is estimated by tracking the brightness variation at each pixel, as shown in FIG. 7. The lower bound of the wave velocity error will be formulated, and an example with realistic values will be given.

According to equation (6), the modulation wave equation is $$|P(x,t)|^2 = f(x)^2 + A^2 - 2A \cdot f(x) \cos(\Delta\omega t - s(x)) \quad (12)$$

At a given location $x_0$, the pixel value is $$B(t) = f(x_0)^2 + A^2 - 2A \cdot f(x_0) \cos(\Delta\omega t - s(x_0)) \quad (13)$$

Assuming that the signal includes white Gaussian noise, the discrete pixel value over multiple observations (multiple frames of the wave video) can be written as $$x[n] = C + D \cdot \cos(\Delta\omega n + \phi) + w[n] \quad (14)$$

where $C = f(x_0)^2 + A^2$, $D = -2A \cdot f(x)$, $\phi = -s(x_0)$ and $w[n] = \mathcal{N}(0, \sigma^2)$, a zero mean Gaussian distribution with standard deviation $\sigma$. Therefore, the likelihood function is $$p(x; \phi) = \frac{1}{(2\pi\sigma^2)^{\frac{N}{2}}} \cdot \exp\left(-\frac{1}{2\sigma^2} \sum_{n=0}^{N-1}(x[n] - C - D \cdot \cos(\Delta\omega n + \phi))\right) \quad (15)$$

Taking the first and second derivatives of the natural logarithm of the likelihood function yields:

$$\frac{\partial p(x; \phi)}{\partial \phi} = -\frac{1}{\sigma^2} \cdot \sum_{n=0}^{N-1} [x[n] - C - D \cdot \cos(\Delta\omega n + \phi)] \cdot D\sin(\Delta\omega n + \phi) \quad (16)$$

and $$\frac{\partial^2 p(x; \phi)}{\partial \phi^2} = -\frac{D}{\sigma^2} \cdot \sum_{n=0}^{N-1} [(x[n] - C) \cdot \cos(\Delta\omega n + \phi) - D\cos(2\Delta\omega n + 2\phi)] \quad (17)$$

Taking the negative expected value gives $$-E\left[\frac{\partial^2 p(x; \phi)}{\partial \phi^2}\right] = \frac{D}{\sigma^2} \cdot \sum_{n=0}^{N-1} [(x[n] - C) \cdot \cos(\Delta\omega n + \phi) - D\cos(2\Delta\omega n + 2\phi)]$$

$$= \frac{D}{\sigma^2} \cdot \sum_{n=0}^{N-1} [D\cos^2(\Delta\omega n + \phi) - D\cos(2\Delta\omega n + 2\phi)]$$

$$= \frac{D^2}{\sigma^2} \cdot \sum_{n=0}^{N-1} \left[\frac{1}{2} + \frac{1}{2}\cos(\Delta\omega n + \phi) - \cos(2\Delta\omega n + 2\phi)\right] \quad (18)$$

If an integer or half integer number of cycles is acquired in experiments by choosing $\Delta\omega N = m\pi$, m being an integer, then the expected value of the cosine term is zero:

$$E[\cos(2\Delta\omega n + 2\phi)] = 0 \quad (19)$$

Thus, $$-E\left[\frac{\partial^2 p(x;\phi)}{\partial \phi^2}\right] = \frac{ND^2}{2\sigma^2} \quad (20)$$

The inverse of equation (20) gives the Cramer-Rao lower bound of the phase estimation:

$$\text{var}(\hat{\phi}) \geq \frac{1}{-E\left[\frac{\partial^2 p(x;\phi)}{\partial \phi^2}\right]} = \frac{2\sigma^2}{ND^2} \quad (21)$$

The local shear wave velocity estimation is equivalent to estimating the local slope of the phase function. At that stage, the tradeoff of image resolution and estimation accuracy has to be considered. If the image resolution is set to be M pixels, the accuracy of the slope estimation of bounded by a function of M. If the problem is modeled as a line fitting problem, and the phase function is assumed to be in the form of:

$$\phi[m] = F + G \cdot m + w[m] \quad (22)$$

where w[m] is a zero mean Gaussian distribution with variance determined by equation (21), with independent observations at those M pixels, than the slope estimation G can be obtained with variance $$\text{var}(\hat{G}) \geq \frac{12 \cdot \text{var}(\hat{\phi})}{M(M^2 - 1)} \quad (23)$$

Because stiff regions are generally more important than the normal background, more attention is to be paid to the estimator accuracy in the stiff regions. The vibration amplitude is low in those regions because of the sonoelastography effect; thus, the signal-to-noise ratio (SNR) is also low. An empirical estimate of the SNR in the stiff regions is one. In the experiments, a typical number of frames of the shear wave propagation video is 60. Thus, in equation (21), the variance of the phase estimation is approximately 1/30.

M in equation (23) refers to the number of independent measurements. The ultrasound scanner determines that only one independent measurement can be made within the width of the point spread function. A point spread function is simulated with the Field II tool box. The imaging system parameters are selected from a typical experimental setting and are summarized in Table I below:

TABLE I

| Parameter | Value |
|---|---|
| Sampling frequency | $150 \times 10^6$ Hz |
| Speed of sound | 1540 m/s |
| Central frequency | $7.5 \times 10^6$ Hz |
| Relative bandwidth | 30% |
| Number of elements | 128 |
| F number | 3 |

Figure 8:
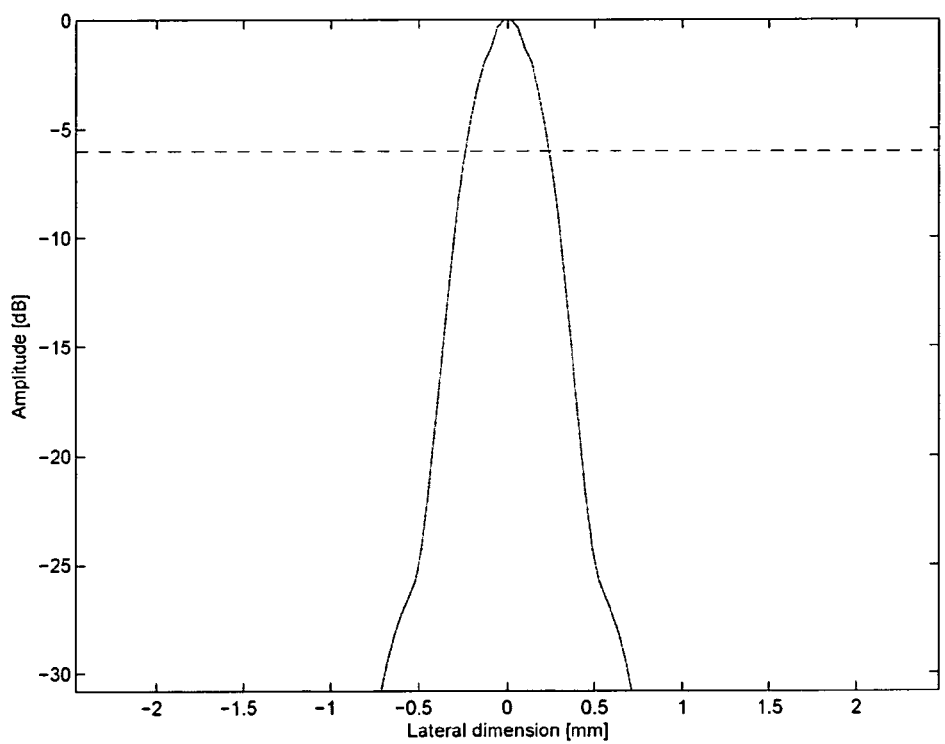
FIG. 8 is a graph of an ultrasound scanner's estimated point spread function.

The simulation shows that the 6 dB width of the point spread function in the lateral direction is approximately 0.5 mm, as shown in FIG. 8. Assuming a realistic shear wave speed of 4 m/s and a driving frequency of 200 Hz, the relation between the elasticity estimation resolution and the estimation relative error will be discussed.

If the resolution is chosen to be 2 mm, there are four independent measurements within that length. According to equation (23), $$\text{var}(\hat{G}) \geq \frac{12 \cdot \text{var}(\hat{\phi})}{M(M^2 - 1)} \quad (24)$$

$$= \frac{12 \cdot 1/30}{4(4^2 - 1)}$$

$$= 0.0067$$

Since the phase increase is $2\pi$ over one shear wave wavelength, the phase slope may be estimated in terms of the wavelength $\lambda$ by:

$$slope_\phi = 2\pi/\lambda$$

$$= 2\pi/(20*2)$$

$$= 0.1571$$

Thus, the relative error is 4%.

Figure 9:
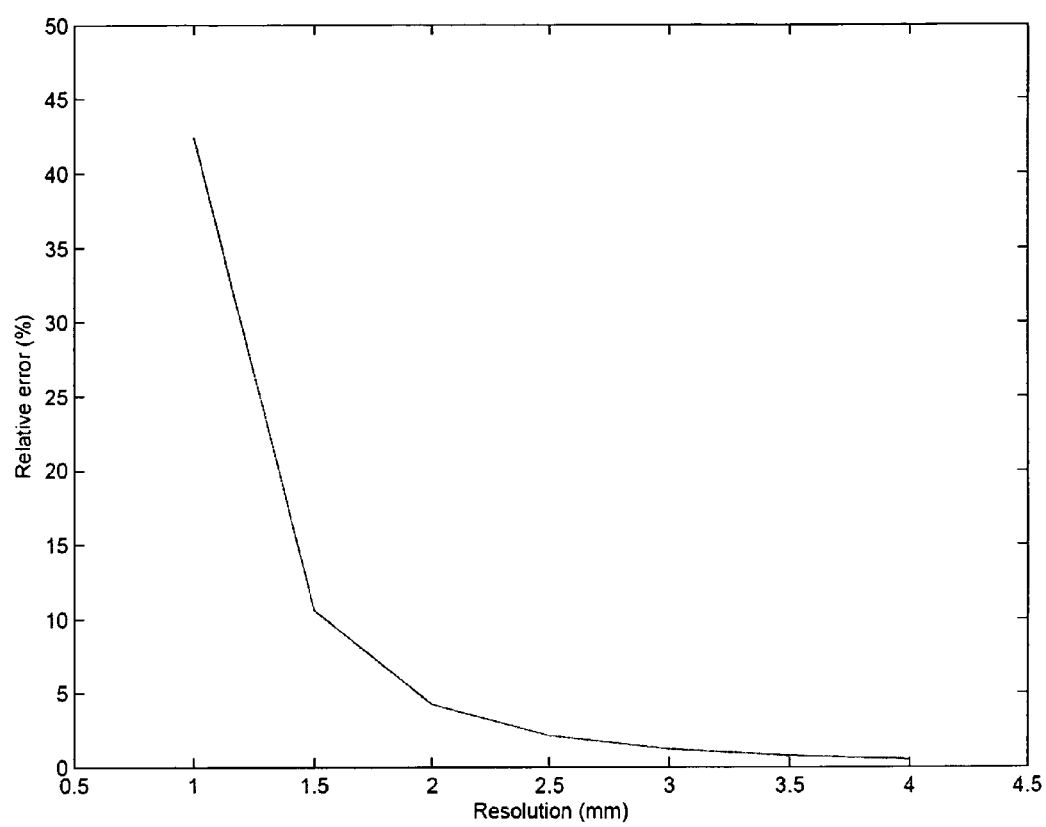
FIG. 9 is a graph of the tradeoff between image resolution and relative error.

The tradeoff between the elasticity image resolution and the estimation relative error is plotted in FIG. 9. Equation (23) provides a lower bound of the estimation accuracy. In practice, that lower bound may not be achievable, and the error in practice may be higher.

Variations of the preferred embodiment are possible. For instance, physical vibration of the ultrasound probe 106 can be replaced with "virtual probe motion," in which the image processing device 110 electronically processes the ultrasound signals from the ultrasound probe 106 at an adjustable frequency to simulate the vibration of the ultrasound probe 106. Such processing can include complex rotation or temporal shifting on the ultrasound signals. In another variation, in addition to or instead of the probe motion, whether physical or virtual, multiple shear wave sources 102 are provided to introduce multiple shear waves at the same or different frequencies to create shear wave interference in the tissue.

While a preferred embodiment and variations thereof have been set forth in detail, those skilled in the art who have reviewed the present disclosure will readily appreciate that other embodiments can be realized within the scope of the invention. For example, numerical values are illustrative rather than limiting, as are disclosures of specific equipment and technology. Therefore, the present invention should be construed as limited only by the appended claims.

We claim:

1. A method for visualizing shear wave propagation in a medium, the method comprising:
   (a) introducing a shear wave from a shear wave source into the medium, the shear wave having a shear wave frequency and a shear wave phase velocity;
   (b) detecting a propagation of the shear wave through the medium by using an ultrasound probe to produce an ultrasound signal;
   (c) introducing a vibration into the ultrasound signal at a second frequency;
   (d) from the ultrasound signal having the vibration, deriving a modulation wave which represents a propagation of the shear wave relative to the ultrasound probe, the modulation wave having a modulation wave phase velocity which varies as a difference between the shear wave frequency and the second frequency; and (e) producing an image representing the shear wave propagation from the modulation wave derived in step (d).

2. The method of claim 1, wherein step (e) comprises producing an image in real time of the modulation wave.

3. The method of claim 2, wherein step (e) further comprises estimating, from the image of the modulation wave, a local vibration phase at each pixel of the image of the modulation wave.

4. The method of claim 3, wherein a plurality of said images in real time of the modulation wave are produced, and wherein the local vibration phase is estimated from a Fourier transform carried out at a time trace of each pixel from the plurality of images of the modulation wave.

5. The method of claim 3, wherein step (e) further comprises performing a phase unwrapping on the local vibration phase to produce a smooth phase surface.

6. The method of claim 5, wherein step (e) further comprises performing a noise reduction on the smooth phase surface.

7. The method of claim 5, wherein step (e) further comprises converting the smooth phase surface to a wave pattern with an artificially increased spatial density.

8. The method of claim 1, wherein step (c) comprises physically vibrating the ultrasound probe at the second frequency.

9. The method of claim 8, wherein step (b) comprises applying a layer of ultrasound gel between the medium and the ultrasound probe such that the ultrasound probe is acoustically coupled to the medium through the ultrasound gel as the ultrasound probe vibrates.

10. The method of claim 1, wherein step (c) comprises electronically producing an equivalent virtual vibration in the ultrasound signal.

11. The method of claim 1, wherein step (a) comprises introducing multiple shear waves into the medium.

12. A system for visualizing shear wave propagation in a medium, the system comprising:
    a shear wave source for introducing a shear wave into the medium, the shear wave having a shear wave frequency and a shear wave phase velocity;
    an ultrasound probe for detecting a propagation of the shear wave through the medium to produce an ultrasound signal, a vibration at a second frequency being introduced into the ultrasound signal;
    an image processing device, in communication with the ultrasound probe, for deriving, from the ultrasound signal having the vibration, a modulation wave which represents a propagation of the shear wave relative to the ultrasound probe, the modulation wave having a modulation wave phase velocity which varies as a difference between the shear wave frequency and the second frequency, and producing an image representing the shear wave propagation from the modulation wave; and
    an image output device for outputting the image.

13. The system of claim 12, wherein the image output device comprises a display.

14. The system of claim 12, wherein the image processing device produces an image in real time of the modulation wave.

15. The system of claim 14, wherein the image processing device estimates, from the image of the modulation wave, a local vibration phase at each pixel of the image of the modulation wave.

16. The system of claim 15, wherein a plurality of said images in real time of the modulation wave are produced, and wherein the local vibration phase is estimated from a Fourier transform carried out at a time trace of each pixel from the plurality of images of the modulation wave.

17. The system of claim 15, wherein the image processing device estimates the local vibration phase by performing a phase unwrapping on the local vibration phase to produce a smooth phase surface.

18. The system of claim 16, wherein the image processing device performs a noise reduction on the smooth phase surface.

19. The system of claim 17, wherein the image processing device converts the smooth phase surface to a wave pattern with an artificially increased spatial density.

20. The system of claim 12, wherein the ultrasound probe is physically vibrated at the second frequency.

21. The system of claim 12, wherein an equivalent virtual vibration is electronically produced in the ultrasound signal.

22. The system of claim 12, wherein the shear wave source introduces multiple shear waves into the medium.

23. A method for visualizing shear wave propagation in a medium, the method comprising:
    (a) introducing a shear wave from a shear wave source into the medium, the shear wave having a shear wave frequency and a shear wave phase velocity;
    (b) detecting a propagation of the shear wave through the medium by using an ultrasound probe to produce an ultrasound signal;
    (c) introducing, at a second frequency, at least one of (i) a vibration into the ultrasound signal and (ii) a second shear wave into the medium;
    (d) from the ultrasound signal, deriving a modulation wave which represents a propagation of the shear wave relative to the ultrasound probe, the modulation wave having a modulation wave phase velocity which varies as a difference between the shear wave frequency and the second frequency; and
    (e) producing an image representing the shear wave propagation from the modulation wave derived in step (d), wherein step (e) comprises:
        (i) producing an image in real time of the modulation wave; and
        (ii) estimating, from the image of the modulation wave, a local vibration phase at each pixel of the image of the modulation wave.

24. The method of claim 23, wherein the local vibration phase is estimated from a Fourier transform carried out at each pixel of the image of the modulation wave.

25. The method of claim 23, wherein step (e) further comprises performing a phase unwrapping on the local vibration phase to produce a smooth phase surface.

26. The method of claim 25, wherein step (e) further comprises performing a noise reduction on the smooth phase surface.

27. The method of claim 25, wherein step (e) further comprises converting the smooth phase surface to a wave pattern with an artificially increased spatial density.

28. A system for visualizing shear wave propagation in a medium, the system comprising:
    a shear wave source for introducing a shear wave into the medium, the shear wave having a shear wave frequency and a shear wave phase velocity;
    an ultrasound probe for detecting a propagation of the shear wave through the medium to produce an ultrasound signal;
    means for introducing, at a second frequency, at least one of (i) a vibration into the ultrasound signal and (ii) a second shear wave into the medium;

an image processing device, in communication with the ultrasound probe, for deriving, from the ultrasound signal having the vibration, a modulation wave which represents a propagation of the shear wave relative to the ultrasound probe, the modulation wave having a modulation wave phase velocity which varies as a difference between the shear wave frequency and the second frequency, and producing an image representing the shear wave propagation from the modulation wave; and an image output device for outputting the image, wherein the image processing device produces an image in real time of the modulation wave and estimates, from the image of the modulation wave, a local vibration phase at each pixel of the image of the modulation wave.

29. The system of claim 28, wherein the local vibration phase is estimated from a Fourier transform carried out at each pixel of the image of the modulation wave.

30. The system of claim 28, wherein the image processing device estimates the local vibration phase by performing a phase unwrapping on the local vibration phase to produce a smooth phase surface.

31. The system of claim 30, wherein the image processing device performs a noise reduction on the smooth phase surface.

32. The system of claim 31, wherein the image processing device converts the smooth phase surface to a wave pattern with an artificially increased spatial density.

* * * * *